United States Patent [19]

Sowinski et al.

[11] 3,957,769

[45] May 18, 1976

[54] 1,2,4-BENZOTHIADIAZINES

[75] Inventors: Francis A. Sowinski, Edison, N.J.; B. Richard Vogt, Yardley, Pa.

[73] Assignee: E. R. Squibb & Sons, Inc., Princeton, N.J.

[22] Filed: Nov. 23, 1973

[21] Appl. No.: 418,496

[52] U.S. Cl. .............................. 260/243 D; 424/246
[51] Int. Cl.² ....................................... C07D 285/24
[58] Field of Search ................................ 260/243 D

[56] References Cited
UNITED STATES PATENTS

| | | | |
|---|---|---|---|
| 3,133,918 | 5/1964 | MacPhillamy et al. | 260/243 D |
| 3,163,644 | 12/1964 | de Stevens et al. | 260/243 D |
| 3,163,645 | 12/1964 | de Stevens et al. | 260/243 D |
| 3,252,975 | 5/1966 | de Stevens et al. | 260/243 D |

OTHER PUBLICATIONS

Cohnen et al., Chem. Ber. 105 pp. 757–769 (1972).
Cohnen et al., Chem. Ber. 106 pp. 3368–3375 (1973).
Barnes et al., Chem. Comm. 1973 (20) 776–777.

*Primary Examiner*—Paul M. Coughlan, Jr.
*Attorney, Agent, or Firm*—Lawrence S. Levinson; Merle J. Smith; Donald J. Barrack

[57] ABSTRACT

Novel 1,2,4-benzothiadiazines substituted with an amino, alkylamino, or dialkylamino group in the 3-position are useful as central nervous system depressants and as diuretics.

10 Claims, No Drawings

1,2,4-BENZOTHIADIAZINES

BRIEF DESCRIPTION OF THE INVENTION

Compounds having the structure:

I 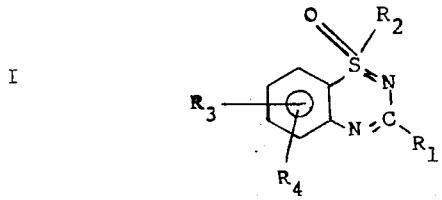

and their pharmaceutically acceptable acid-addition salts, have useful pharmacological activities. In formula I, and throughout the specification, the symbols are as defined below:

$R_1$ is amino, alkylamino, or dialkylamino;

$R_2$ is phenyl or phenyl substituted with halogen, nitro, trifluoromethyl, alkyl, or alkoxy;

$R_3$ is hydrogen, halogen, nitro, cyano, trifluoromethyl, alkyl, or alkoxy; and $R_4$ is hydrogen or

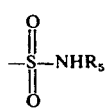

($R_5$ is hydrogen or alkyl);

The term "alkyl" refers to alkyl groups having 1 to 8 carbon atoms. The alkyl groups may be either straight chained or branched, e.g., methyl, ethyl, propyl, isopropyl, tert-butyl, pentyl, isooctyl, and the like. Alkyl groups of 1 to 3 carbon atoms are preferred.

The term "alkoxy" refers to groups having the formula Y—O— wherein Y is alkyl as defined above.

The term "halogen" refers to fluorine, chlorine, bromine, and iodine; fluorine, chlorine and bromine are preferred.

DETAILED DESCRIPTION OF THE INVENTION

The compounds of formula I are central nervous system depressants and may be used as tranquilizers for the relief of anxiety and tension states, for example in mice, rats, dogs and other mammalian species, in the same manner as chlordiazepoxide. For this purpose these compounds may be incorporated in a conventional dosage form such as tablet, capsule, injectable or the like, along with the necessary carrier material, excipient, lubricant, buffer or the like, for oral or parenteral administration in single or divided doses of about 1 to 100 mg./kg./day, preferably about 5 to 15 mg./kg., two to four times daily.

The compounds of formula I are diuretics, and as such, are useful in the treatment of hypertension in mammals. They may be formulated in conventional dosage form such as tablet, capsule, injectable or the like, along with the necessary carrier material, excipient, lubricant, buffer or the like, for oral or parenteral administration in single or divided doses of from about 1 to 100 mg./kg./day, preferably 3 to 12 mg./kg./day.

The compounds of formula I wherein $R_4$ is hydrogen are prepared using acids having the formula:

II 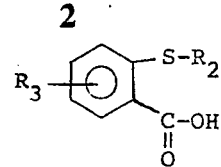

as the starting material. Compounds of formula II are known; see, for example, Coll. Czech. Chem. Commun., 33, 1852 (1968), J. Org. Chem., 38, 20 (1973) and references cited therein.

The acid of formula II is converted to the corresponding acid chloride having the formula:

III 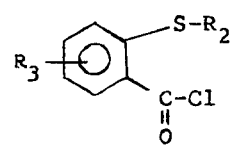

using means well known in the art. For example, an acid of formula II may be reacted with either thionyl chloride, phosphorous trichloride, or phosphorous pentachloride. The conversion may be carried out in an organic solvent, e.g., benzene, at elevated temperatures.

The acid chloride of formula III can be converted to an acetophenone derivative having the formula:

IV 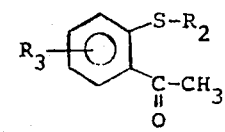

by reacting it with ethoxy-magnesium diethyl malonate in an inert organic solvent, such as ethyl ether, under reflux conditions for a period of time ranging from about 1 hour to 24 hours, preferably 2 hours to 4 hours, and subsequently hydrolyzing the resulting complex with dilute sulfuric acid and heating to decarboxylate the intermediate acylation product.

The compound of formula IV is oxidized to the corresponding sulfoxide, i.e.,

V 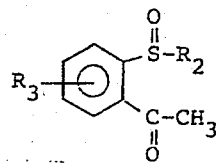

using a mild, selective oxidizing agent such as sodium periodate. The oxidation reaction is run at a temperature of from about 0°C to 85°C, preferably 30°C to 50°C, for about 24 hours to 15 days, preferably 5 days to 7 days, in an organic solvent such as glyme.

Reaction of the 2-(substituted sulfinyl)acetophenone of formula V with hydrazoic acid yields a mixture of products having the formulas:

VI 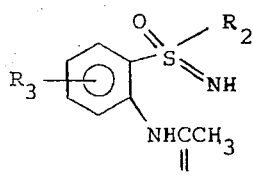

and

VII 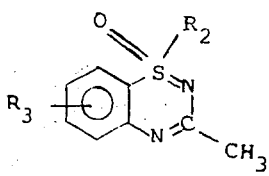

The reaction is run in an organic solvent, preferably a halogenated hydrocarbon such as chloroform, at a temperature of from about 31 30° to +55 °C, preferably 30° to 50°C. In addition to the hydrazoic acid, a strong mineral acid such as sulfuric acid, is also present.

The product mixture made up of compounds of formulas VI and VII is hydrolized to yield a 2-(substituted sulfonimidoyl) aniline derivative having the formula:

VIII 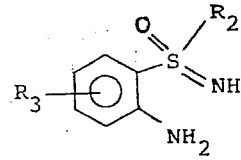

The hydrolysis reaction is carried out under reflux conditions in an aqueous solution of base such as sodium or potassium hydroxide. The compound of formula VIII is converted into an acid-addition salt, preferably one that is physiologically acceptable. Exemplary salts are the hydrohalides, sulfate, nitrate, phosphate, tartrate, maleate, fumarate, citrate, succinate, methanesulfonate, benzenesulfonate, toluenesulfonate and the like.

Ring closure of the acid-addition salt of the compound of formula VIII is accomplished by reacting the salt with 1,1'-carbonyldiimidazole in an inert organic solvent, such as, o-dichlorobenzene at reflux temperature for about 1 hour to 24 hours, preferably 1 hour to 3 hours. The resulting compound has the structure:

IX 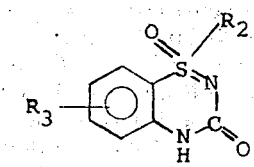

Reaction of the 1,2,4-benzothiadiazin-3(4H)-one, 1-oxide of formula IX with phosphorous oxychloride yields a compound having the structure:

X 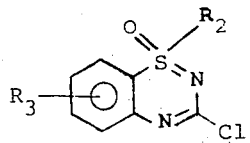

The substituted 1,2,4-benzothiadiazin-3(4H)-one, 1-oxide of formula IX is suspended in the phosphorous oxychloride, a small amount of water is added, and the mixture is heated under reflux conditions for about 5 minutes to 24 hours, preferably about 30 minutes to 2 hours.

The 3-chloro-1,2,4-benzothiadiazine, 1-oxide of formula X can be reacted with an amine having the formula

XI R₁H to yield the compound of formula I wherein R₄ is hydrogen, i.e., compounds of the formula XII 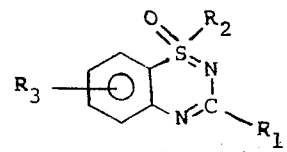

Reaction of a 3-chloro-1,2,4-benzothiadiazine, 1-oxide of formula X with an amine of formula XI is carried out in an organic solvent such as glyme under reflux conditions. The reaction is continued for about 1 hour to 24 hours, preferably 6 hours to 10 hours.

Compounds of formula I wherein $R_4$ is $$-\overset{O}{\underset{O}{\overset{\|}{S}}}-NHR_5$$

are obtained using compounds of the formula:

XIII $R_3$—⟨⟩—S—$R_2$
         NH₂ as starting materials. The compounds of formula XIII are prepared using methods described in Chem. Ber., 39, 3597ff (1906) and in U.S. Pat. No. 3,188,320 issued June 8, 1965 to Sowinski et al.

The aniline derivative of formula XIII is first reacted with acetic anhydride under reflux conditions for about 5 minutes to 8 hours, preferably 15 minutes to 1 hour. The reaction is run in an organic solvent, preferably a halogenated hydrocarbon such as chloroform. A base such as pyridine is added to the reaction mixture. The resulting acetanilide has the formula:

XIV 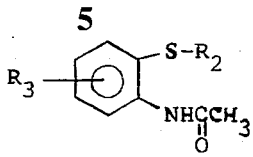

The acetanilide of formula XIV is reacted with chlorosulfonic acid in an organic solvent such as o-dichlorobenzene at a temperature of from about 0° to 180°C, preferably 120° to 150°C for a period of time ranging from about 10 minutes to 16 hours, preferably 1 hour to 3 hours, and yields a chlorosulfonyl substituted acetanilide having the formula:

XV 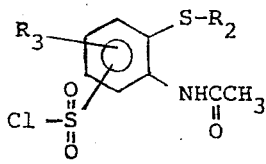

Compounds having the formula

XVI 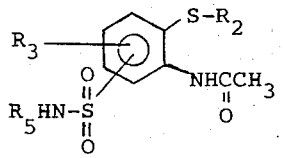

are prepared by reacting a chlorofulfonyl substituted acetanilide of formula XV with a compound of the formula

XVII                 NH₂R₅

When $R_5$ is hydrogen, the compound of formula XV is dissolved in an aromatic hydrocarbon, such as benzene, and added slowly to a concentrated solution of aqueous ammonia. The chlorosulfonyl acetanilide solution is added to the ammonia at a temperature of from about 0° to 80°C, preferably 5° to 10°C. After the addition is completed, the reaction mixture is heated to reflux temperature and then stirred for a period of time ranging from about 1 hour to 24 hours, preferably 1 hour to 3 hours. When $R_5$ is alkyl, the compound of formula XV is dissolved in an organic solvent, such as benzene, and the solution is then added to an ice-cooled aqueous solution of the amine of formula XVII. After a short period, the reaction mixture is heated under reflux for a period of about 30 minutes to 12 hours, preferably about 1 to 3 hours.

The substituted acetanilide of formula XVI is oxidized using a mild, selective oxidizing agent such as sodium periodate to yield a compound of the formula:

XVIII 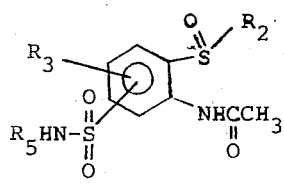

Reaction may be carried out in glyme by slowly adding an aqueous solution of the oxidizing agent to the sulfamylacetanilide. Following completion of the addition of the oxidizing agent, the mixture is stirred for a period of time ranging from 24 hours to 240 hours, preferably 72 hours to 120 hours, while heating under reflux conditions.

The compound of formula XVIII is hydrolized using an aqueous solution of base such as potassium or sodium hydroxide. The compound of formula XVIII is dissolved in an aqueous base and heated at reflux temperature for a period of time ranging from 1 hour to 5 hours, preferably 2 hours to 4 hours. The product has the formula:

IXX 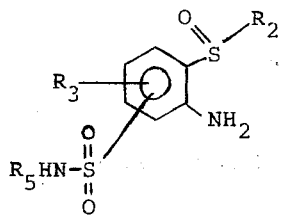

The compound of formula IXX is reacted with hydrazoic acid in an organic solvent, preferably a halogenated hydrocarbon such as chloroform, at a temperature of from about −30° to 55°C, preferably 30° to 50°C. In addition to the hydrazoic acid, a mineral acid such as sulfuric acid, is also present. The resultant product has the formula:

XX 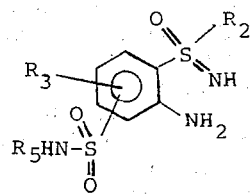

Ring closure of the compound of formula XX is accomplished by reacting the compound with 1,1′-carbonyldiimidazole and a halogenated aromatic solvent such as o-dichlorobenzene at reflux temperature for about 1 hour to 24 hours, preferably 1 hour to 2 hours. The resultant compound has the structure:

XXI 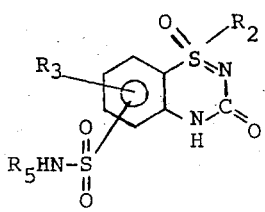

Reaction of the 1,2,4-benzothiadiazin-3(4H)-one, 1-oxide of formula XXI with phosphorous oxychloride yields a compound having the structure:

XXII 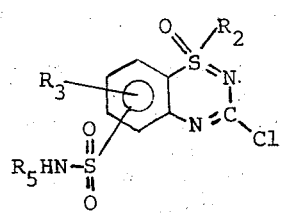

The 1,2,4-benzothiadiazin-3 (4H)-one, 1-oxide of formula XXI is suspended in the phosphorus oxychloride, a small amount of water is added, and the mixture is heated under reflux conditions for about 5 1 minutes to 24 hours, preferably about 30 minutes to 2 hours.

The 3-chloro-1,2,4-benzothiadiazine, 1-oxide of formula XXII can be reacted with an amine having the formula

XI  $R_1H$ to yield the compound of formula I wherein $R_4$ is

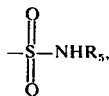

i.e., compounds of the formula

XXIII 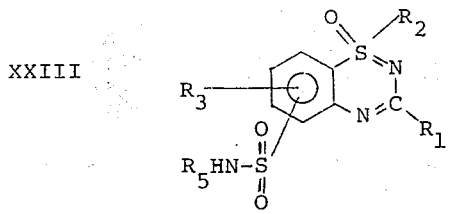

Reaction of a 3-chloro-1,2,4-benzothiadiazine, 1-oxide of formula XXII with an amine of formula XI is carried out in an organic solvent such as glyme under reflux conditions. The reaction is continued for about 1 hour to 24 hours, preferably 6 hours to 10 hours.

Formation of the pharmaceutically acceptable acid-addition salts of the compounds of formula I may be accomplished by methods well known in the art. Both organic and inorganic acids are specifically contemplated. Illustrative acids are the hydrohalides, especially the hydrochloride and hydrobromide, sulfate, nitrate, phosphate, tartrate, maleate, fumarate, citrate, succinate, methanesulfonate, benzenesulfonate, toluenesulfonate, and the like.

Exemplary of compounds having the structure

XII 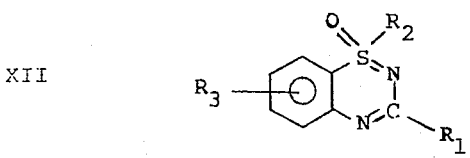

are:
7-chloro-3-amino-1-phenyl-1,2,4-benzothiadiazine-1-oxide;
3-ethylamino-1-phenyl-1,2,4-1 -benzothiadiazine-1-oxide;
6-nitro-3-dimethylamino-1-phenyl-1,2,4,-benzothiadiazine-1-oxide;
7-cyano-3-amino-1-phenyl-1,2,4-benzothiadiazine-1-oxide;
7-trifluoromethyl-3-isopropylamino-1-phenyl-1,2,4-benzothiadiazine-1-oxide;
7-methyl-3-diethylamino-1-phenyl-1,2,4-benzothiadiazine-1-oxide;
7-methoxy-3-methylamino-1-phenyl-1,2,4-benzothiadiazine-1-oxide;
7-chloro-3-amino-1-(2-chlorophenyl)-1,2,4-benzothiadiazine-1-oxide;
3-amino-1-(2-nitrophenyl)-1,2,4-benzothiadiazine-1-oxide;
7-chloro-3-dimethylamino-1-(4-trifluoromethylphenyl)-1,2,4-benzothiadiazine-1-oxide;
7-nitro-3-methylamino-1-(4-ethylphenyl)-1,2,4-benzothiadiazine-1-oxide;
7-bromo-3-amino-1-1-(4-methoxyphenyl)-1,2,4-benzothiadiazine-1-oxide.

Exemplary of compounds having the structure

XXIII 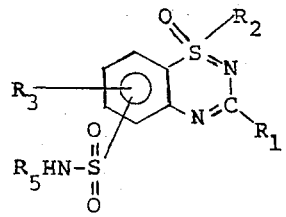

are:
6-chloro-3-amino-1-phenyl-7-sulfamyl-1,2,4-1 -benzothiadiazine-1-oxide;
6-chloro-3-methylamino-1-(2-chlorophenyl)-7-methylsulfamyl-1,2,4-benzothiadiazine-1-oxide;
3-diethylamino-1-(4-methoxyphenyl)-7-sulfamyl-1,2,4-benzothiadiazine-1-oxide;
6-nitro-3-amino-1-(4-ethylphenyl)-7-sulfamyl-1,2,4-benzothiadiazine-1-oxide;
6-trifluoromethyl-3-methylamino-1-(4-trifluoromethylphenyl)-7-methylsulfamyl-1,2,4-benzothiadiazine-1-oxide;
6-nitro-3-amino-1-(2-nitrophenyl)-7-sulfamyl-1,2,4-benzothiadiazine-1-oxide;
6-cyano-3-amino-1-phenyl-b 7-sulfamyl-1,2,4-benzothiadiazine-1-oxide;
6-methyl-3-methylamino-1-phenyl-7-methylsulfamyl-1,2,4-benzothiadiazine-1-oxide;
6-methoxy-3-dimethylamino-1-phenyl-7-sulfamyl-1,2,4-benzothiadiazine-1-oxide.

The following examples further illustrate the invention.

EXAMPLE 1

7-Chloro-3-methylamino-1-phenyl-1,2,4-benzothiadiazine-1-oxide, hydrochloride (1:1), hydrate (1:1)

A. 4-Chloro-2-(phenylthio)benzoyl chloride

To a stirred suspension of 59.2 g. (0.224 mole) of 4-chloro-2-(phenylthio)benzoic acid in 200 ml. of benzene is added dropwise 41.6 g. (0.35 mole) of thionyl chloride during a 1 hour period, and the reaction mixture is heated under reflux for an additional hour. The reaction mixture is then concentrated to dryness under reduced pressure, and the residue is recrystallized from 300 ml. of boiling hexane to yield 41.9 g. of pale yellow product, melting point 94°–96°C.

Anal. Calcd for $C_{13}H_8Cl_2OS$: C, 55.13; H, 2.85; Cl, 25.04. Found; C, 55.37; H, 2.73; Cl, 24.81.

B. 4-Chloro-2-(phenylthio)acetophenone

A stirred mixture of 3.76 g (0.156 gram-atom) of magnesium turnings, 5 ml. of absolute ethanol, and a few drops of carbon tetrachloride is warmed until the reaction has been initiated. A mixture of 25.0 g. (0.155 mole) of diethylmalonate, 9.3 ml. (0.31 mole in toto) of absolute alcohol, and 150 ml. of anhydrous ether is added rapidly. A gummy reaction product separates from solution. This is heated under reflux conditions for 3 hours. A solution of 39.7 g. (0.14 mole) of 4-chloro-2-(phenylthio) benzoyl chloride in 200 ml. of ether is then run in rapidly from a dropping funnel. After stirring for an additional 3 hours, the complexed addition product is decomposed with a solution of 25 ml. of concentrated sulfuric acid in 200 ml. of water. The addition product is then extracted into 500 ml. of chloroform, and the chloroform extract dried and concentrated to give a solid, melting point 106°–108°C. This solid is heated in a mixture of 20 ml. of concentrated sulfuric acid, 50 ml. of water, and 200 ml. of acetic acid under reflux conditions for 2 hours. The acetic acid is then substantially removed by distillation under reduced pressure. Addition of a further 100 ml. portion of water and cooling leads to crystallization of 35.8 g. of the ketone, melting point 65°–66°C, after recrystallization from aqueous alcohol.

Anal. Calcd for $C_{14}H_{11}ClOS$: C, 63.98; H, 4.22; Cl, 13.40. Found: C, 63.79; H, 4.46; Cl, 13.40.

C. 4-Chloro-2-(phenylsulfinyl)acetophenone

To a vigorously stirred solution of 199 g. (0.75 mole) of 4-chloro-2-(phenylthio)acetophenone in 2 liters of 1,2-dimethoxyethane (glyme) is added a solution of 175.5 g. (0.825 mole) of sodium periodate; the mixture is heated at 40°C for 7 days. The mixture is then filtered from the inorganic materials and the glyme distilled from the filtrate to give a slurry of crystals. These are filtered and this mixture of sulfoxide and starting material is separated from the inorganic contaminants by extraction into abs. ethanol. After filtration and concentration, the residue is dissolved in 1.5 liters of boiling hexane to give (after cooling and filtration) 91.8 g. of product, melting point 129°–130°C.

Anal. Calcd for $C_{14}H_{11}ClO_2S$: C, 60.33; H, 3.97; S, 11.50. Found: C, 60.07; H, 4.18; S, 11.74.

D. 4-Chloro-2-(phenylsulfonimidoyl)acetanilide and 7-chloro-3-methyl-1-phenyl-1,2,4-benzothiadiazine-1-oxide A stirred, cooled (0°C) solution of 7.0 g. (0.025 mole) of 4-chloro-2-(phenylsulfinyl)acetophenone in 100 ml. of chloroform is combined with 14.0 ml. of concentrated sulfuric acid and treated dropwise with 69 ml. (0.075 mole) of a 1.08 N chloroform solution of hydrazoic acid. After stirring for 1 hour, the ice bath is removed and the mixture is warmed to 40°C; stirring is continued for an additional 30 minutes. The reaction mixture is then cooled, added to 100 ml. of ice water, neutralized with solid sodium bicarbonate, the chloroform layer separated, and, after drying over anhydrous magnesium sulfate, concentrated to dryness. On recrystallization from aqueous alcohol, the residue gives 3.6 g. of 4-chloro-2-(phenylsulfonimidoyl) acetanilide, melting point 141°–142°C.

Anal. Calcd for $C_{14}H_{13}ClN_2O_2S \cdot \frac{1}{2} H_2O$: C, 52.90; H, 4.44; N, 8.82; S, 10.09. Found: C, 53.24; H, 4.18; N, 8.45; S, 10.53.

On standing, the mother liquors from the above recrystallization deposit 0.6 g of 7-chloro-3-methyl-1-phenyl-1,2,4-benzothiadiazine-1-oxide, melting, point 151°–152°C. Anal. Calcd for $C_{14}H_{11}ClN_2OS$: C, 57.84; H, 3.81; N, 964. Found C, 57.75; H, 4.07; N, 9.61.

E. 4-Chloro-2-(phenylsulfonimidoyl)aniline hydrochloride

Following the procedure of (D) but using 83.8 g. (0.30 mole) of 4-chloro-2-(phenylsulfinyl)acetophenone, 500 ml. of chloroform, 250 ml. of concentrated sulfuric acid, and 472 ml. of a 1.4 N chloroform solution of hydrazoic acid, 79.7 g. of a mixture of 4-chloro-2-(phenylsulfonimidoyl)acetanilide and 7-chloro-3-methyl-1-phenyl-1,2,4-benzothiadiazine-1-oxide is obtained. This mixture is stirred and heated under reflux conditions in 450 ml. of 10% sodium hydroxide solution for 3.5 hours. After the mixture is cooled, it is extracted with 500 ml. of chloroform, and the extract is dried and concentrated to give 68.7 g. of a viscous oil. This is extracted with 500 ml. of anhydrous ether. The extract is filtered and cooled in ice. While the extract is cooling in ice, it is treated in a dropwise manner with a slight excess (to pH 4.0) of ethereal hydrogen chloride to give 55.2 g. of product, melting point 217°–219°C after filtration and drying.

F. 7-Chloro-1-phenyl-1,2,4-benzothiadiazin-3(4H)-one, 1-oxide

A stirred mixture of 18.80 g. (0.062 mole) of 4-chloro-2-(phenylsulfonimidoyl)aniline hydrochloride and 10.6 g. (0.065 mole) of 1,1′-carbonyldiimidazole in 500 ml. of o-dichlorobenzene is heated under reflux conditions for 2 hours, filtered, and cooled. The glistening plates which form are filtered, washed with water, and dried to yield 11.28 g. of product, melting point 261°–262°C.

A sample for analysis is recrystallized from alcohol and the melting point is unchanged.

Anal. Calcd for $C_{13}H_{10}ClN_2O_2S$: C, 53.33; H, 3.10; N, 9.57. Found: C, 53.43; H, 3.22; N. 9.74.

G. 3,7-Dichloro-1-phenyl-1,2,4-benzothiadiazine-1-oxide

A suspension of 2.92 g (0.01 mole) of 7-chloro-1-phenyl-1,2,4-benzothiadiazin-3(4H)-one-1-oxide in 25 ml of phosphorus oxychloride is treated with 0.5 ml of water and the mixture is heated under reflux for 45 minutes. The solution is then cooled and poured into 100 ml of a mixture of ice and water. The soluble oily material is taken up in chloroform, the chloroform solution dried, filtered, concentrated, and the residual material recrystallized from acetonitrile to give 0.85 g of colorless product, melting point 162°–164°C.

Anal. Calcd for $C_{13}H_8Cl_2N_2OS$: C, 50.17; H, 2.63; Cl, 22.77; N, 9.01. Found: C, 49.92; H, 2.89; Cl, 22.49; N, 8.66.

H. 7-Chloro-3-methylamino-1-phenyl-1,2,4-benzothiadiazine-1-oxide, hydrochloride (1:1), hydrate (1:1)

To a stirred mixture of 5.14 g. (0.66 mole) of 40% aqueous methylamine solution and 50 ml of glyme is added, over a 30 minute period, a solution of 10.41 g. of 3,7-dichloro-1-phenyl-1,2,4-benzothiadiazine-1-oxide in 150 ml of glyme. The reaction mixture is then heated under reflux for 10 hours, cooled, concentrated to dryness and suspended in 100 ml of 10% hydrochloric acid. The insoluble solid material is filtered, dried and recrystallized from abs. ethanol to give 4.1 g of 7-chloro-3-methylamino-1-phenyl-1,2,4-benzothiadiazin-3(4H)-one-1-oxide, hydrochloride (1:1), hydrate (1:1). Concentration of the filtrate and recrystallization of the residue from acetonitrile gives 2.4 g of product, melting point 248°–249°C, dec.

Anal. Calcd for $C_{14}H_{12}ClN_3OS \cdot HCl \cdot H_2O$: C, 46.67; H, 4.20; N, 11.66. Found: C, 46.96; H, 4.18; N, 11.62.

EXAMPLE 2

6-Chloro-3-methylamino-1-phenyl-7-sulfamyl-1,2,4-benzothiadiazine-1-oxide, hydrochloride

A. 5-Chloro-2-(phenylthio)acetanilide

To a stirred solution of 235.7 g. (1 mole) of 5-chloro-2-(phenylthio)aniline (prepareed by the procedure described in U.S. Pat. No. 3,188,320) in 1 liter of chloroform containing 87.0 g. (1.1 mole) of pyridine, 112.3 g. (1.1 mole) of acetic anhydride is added over a 1 hour period. The mixture is heated under reflux for 1 hour. The cooled reaction mixture is then extracted successively with 1 liter portions of N-hydrochloric acid and N sodium carbonate, dried (anhydrous magnesium sulfate), and concentrated to dryness to give the above product.

B. 5-Chloro-4-chlorosulfonyl-2-(phenylthio)acetanilide

A mixture of 250 g. (0.9 mole) of 5-chloro-2-(phenylthio)acetanilide and 116.52 g. (1.0 mole) of chlorosulfonic acid in 2.5 liters of o-dichlorobenzene is heated at 150°–160°C for 2 hours in an oil bath. The reaction mixture is cooled, washed with 1 liter of cold sodium carbonate solution, washed with water and then dried using magnesium sulfate. Removal of the solvent by distillation under vacuum yields the product.

C. 5-Chloro-2-(phenylthio)-4-sulfamylacetanilde

A solution of 276.0 g. (0.75 mole) of 5-chloro-4-chlorosulfonyl-2-(phenylthio)acetanilide in 2 liters of benzene is added dropwise to 1 liter of concentrated aqueous ammonia, with cooling in an ice bath, over a period of 1 hour. After the addition is complete, the ice bath is removed and the mixture is heated to reflux and stirred vigorously for an additional 2 hours. The benzene is removed by steam distillation, the residual material is cooled, the pH is adjusted to 6.5, and the product is filtered and dried.

D. 5-Chloro-2-(phenylsulfinyl)-4-sulfamylacetanilide 231 g. (0.65 mole) of 5-chloro-2-(phenylthio)-4-sulfamylacetanilide is stirred in 3.5 liters of glyme. A solution of 154 g. (0.72 mole) of sodium periodate in 1500 ml. of water is added to the mixture dropwise over a 2 hour period. The mixture is then stirred vigorously for 24 hours while heating under reflux conditions. The reaction mixture is filtered from the inorganic materials, and concentrated under reduced pressure to remove the glyme. The slurry of crystalline material remaining is cooled, filtered, and the solid material extracted with absolute alcohol, filtered to remove insoluble inorganic contaminants, and the extract partially concentrated, cooled, and filtered to yield the product.

E. 5-Chloro-2-(phenylthiosulfinyl)-4-sulfamylaniline

A solution of 186.8 g. (0.5 mole) of 5-chloro-2-(phenylsulfinyl)-4-sulfamylacetanilide in 1.5 liters of 10% aqueous sodium hydroxide is heated under reflux conditions for 3 hours, cooled, the pH adjusted to 6.5–7 with N hydrochloric acid, and the separated product filtered, dried, and recrystallized from ethanol.

F. 5-Chloro-2-(phenylsulfonimidoyl)-4-sulfamylaniline

A stirred, cooled (0°C) solution of 149.0 g (0.45 mole) of 5-chloro-2-(phenylthiosulfinyl)-4-sulfamylaniline in 1.5 liters of chloroform is combined with 300 ml. of concentrated sulfuric acid and treated dropwise with 450 ml. of a 1 N chloroform solution of hydrazoic acid. After stirring for 1 hour, the ice bath is removed and the mixture is warmed to 40°C; stirring is continued for an additional 30 minutes. The reaction mixture is then cooled, added to 100 ml. of ice water, neutralized with solid sodium bicarbonate, the chloroform layer separated, and, after drying over anhydrous magnesium sulfate, concentrated to dryness. Recrystallization from aqueous alcohol yields the product.

G. 6-Chloro-1-phenyl-7-sulfamyl-1,2,4-benzothiadiazine3(4H)-one-1-oxide

A stirred mixture of 34.5 g (0.1 mole) of 5-chloro-2-(phenylsulfonimidoyl)-4-sulfamylaniline and 16.2 g (0.1 mol) of 1,1'-carbonyldiimidazole in 500 ml. of o-dichlorobenzene is heated under reflux conditions for 2 hours, filtered, and cooled, yielding the product.

H. 3,6-Dichloro-1-phenyl-7-sulfamyl-1,2,4-benzothiadiazine-1-oxide

A suspension of 37.2 g. (0.1 mole) of 6-chloro-1-phenyl-7-sulfamyl-1,2,4-benzothiadiazine-3(4H)-one-1-oxide in 250 ml. of phosphorous oxychloride is treated with 5 ml. of water, and the mixture is heated under reflux conditions for 45 minutes. The solution is then cooled and poured into 100 ml. of a mixture of ice and water to yield the product.

I. 6-Chloro-3-methylamino-1-phenyl-7-sulfamyl-1,2,4-benzothiadiazine-1-oxide, hydrochloride To a stirred mixture of 5.14 g. (0.066 mole) of 40% aqueous methylamine solution and 50 ml. of glyme is added, over a 30 minute period, a solution of 13.5 g. (0.035 mole) of 3,6-dichloro-1-phenyl-7-sulfamyl-1,2,4-benzothiadiazine -1-oxide in 150 ml. of glyme. The reaction mixture is heated under reflux for 10 hours, cooled, concentrated to dryness, and suspended in 100 ml. of 10% hydrochloric acid. Filtration of the solid material yields the product.

EXAMPLES 3 – 10

Following the procedure of Example 1, but substituting the compound listed in column I for 4-chloro-2-(phenylthio)benzoic acid, and the compound listed in column II for methylamine, the compound listed in column III is obtained.

| Example | Column I | Column II | Column III |
|---|---|---|---|
| 3 | 4-(trifluoromethyl)-2-(phenylthio)benzoic acid | dimethylamine | 7-trifluoromethyl-3-dimethylamino-1-phenyl-1,2,4-benzothiadiazine-1-oxide |

| Example | Column I | Column II | Column III |
|---|---|---|---|
| 4 | 5-chloro-2-phenylthio benzoic acid | ethylamine | 6-chloro-3-ethylamino-1-phenyl-1,2,4-benzothiadiazine-1-oxide |
| 5 | 4-nitro-2-(phenylthio) benzoic acid | diethylamine | 7-nitro-3-diethylamino-1-phenyl-1,2,4-benzothiadiazine-1-oxide |
| 6 | 4-(trifluoromethyl)-2-(phenylthio)benzoic acid | isopropylamine | 7-triflouromethyl-3-isopropyl-amino-1-phenyl-1,2,4-benzothiadiazine-1-oxide |
| 7 | 4-cyano-2-(phenylthio) benzoic acid | isobutylamine | 7-cyano-3-isobutylamino-1-phenyl-1,2,4-benzothiadiazine-1-oxide |
| 8 | 4-methyl-2-(phenylthio) benzoic acid | octylamine | 7-methyl-3-octylamino-1-phenyl-1,2,4-benzothiadiazine-1-oxide |
| 9 | 4-chloro-2[(2-chlorophenyl)thio]benzoic acid | methylamine | 7-chloro-3-methylamino-1-(2-chlorophenyl)-1,2,4-benzothiadiazine-1-oxide |
| 10 | 2-(phenylthio)benzoic acid | ammonia | 3-amino-1-phenyl-1,2,4-benzothiadiazine-1-oxide. |

EXAMPLES 11 – 15

Following the procedure of Example 2 but substituting the compound listed in column I for 5-chloro-2-(phenylthio)aniline, and the compound listed in column II for methylamine, the compound listed in column III is obtained.

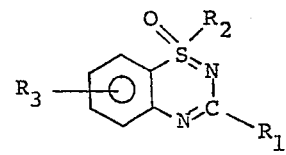

| Example | Column I | Column II | Column III |
|---|---|---|---|
| 11 | 2-(phenylthio)aniline | ammonia | 3-amino-1-phenyl-7-sulfamyl-1,2,4-benzothiadiazine-1-oxide, hydrochloride |
| 12 | 5-nitro-(2-phenylthio) aniline | dimethylamine | 6-nitro-3-dimethylamino-1-phenyl-7-sulfamyl-1,2,4-benzothiadiazine-1-oxide, hydrochloride |
| 13 | 5-cyano-(2-phenylthio) aniline | isopropyl-amine | 6-cyano-3-isopropylamino-1-phenyl-7-sulfamyl-1,2,4-benzothiadiazine-1-oxide, hydrochloride |
| 14 | 5-trifluoromethyl-(2-phenylthio)aniline | octylamaine | 6-trifluoromethyl-3-octylamino-1-phenyl-7-sulfamyl-1,2,4-benzothiadiazine-1-oxide, hydrochloride |
| 15 | 5-methoxy-(2-phenylthio) aniline | methylamine | 6-methoxy-3-methylamino-1-phenyl-7-sulfamyl-1,2,4-benzothiadiazine-1-oxide, hydrochloride. |

What is claimed is:

1. A compound having the structure

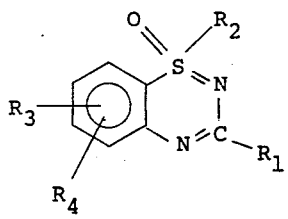

wherein $R_1$ is amino, alkylamino, or dialkylamino; $R_2$ is phenyl or phenyl substituted with halogen, nitro, trifluoromethyl, alkyl or alkoxy; $R_3$ is hydrogen, halogen, nitro, cyano, trifluoromethyl, alkyl, or alkoxy; $R_4$ is hydrogen or

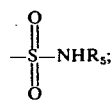

and $R_5$ is hydrogen or alkyl; or a pharmaceutically acceptable acid-addition salt thereof; wherein the terms alkyl and alkoxy refer to groups having 1 to 8 carbon atoms.

2. A compound in accordance with claim 1 having the structure

3. A compound in accordance with claim 1 having the structure

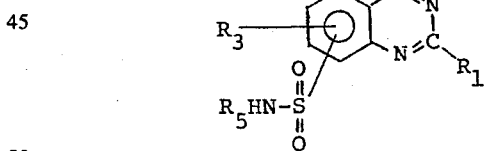

4. A compound in accordance with claim 1 wherein $R_1$ is amino.

5. A compound in accordance with claim 1 wherein $R_1$ is alkylamino.

6. A compound in accordance with claim 1 wherein $R_1$ is dialkylamino.

7. A compound in accordance with claim 1 wherein $R_2$ is phenyl.

8. A compound in acccordance with claim 1 wherein $R_3$ is halogen.

9. A compound in accordance withe claim 8 wherein $R_3$ is chloro.

10. The compound in accordance with claim 1 having the name 7-chloro-3-methylamino-1-phenyl-1,2,4-benzothiadiazine-1-oxide, hydrochloride (1:1), hydrate (1:1).

* * * * *

UNITED STATES PATENT AND TRADEMARK OFFICE
CERTIFICATE OF CORRECTION

PATENT NO. : 3,957,769
DATED : May 18, 1976
INVENTOR(S) : Francis A. Sowinski et al.

It is certified that error appears in the above—identified patent and that said Letters Patent are hereby corrected as shown below:

Column 3, line 25, "31 30°" should read -- -30°C --.

Column 5, line 33, "chlorofulfonyl" should read --chlorosulfonyl--.

Column 7, line 4, "5 1 minutes" should read --5 minutes--.

Column 7, line 57, "1,2,4-1" should read --1,2,4--.

Column 8, line 23, "1,2,4-1" should read --1,2,4--.

Column 8, line 36, "phenyl-b" should read --phenyl- --.

Column 9, line 28, "175.5g." should read --176.5g.--.

Column 11, line 13, "prepareed" should read --prepared--.

Column 11, line 35, "sulfamylacetanilde" should read --sulfamylacetanilide--.

Signed and Sealed this

Thirty-first Day of August 1976

[SEAL]

Attest:

RUTH C. MASON
Attesting Officer

C. MARSHALL DANN
Commissioner of Patents and Trademarks